(12) United States Patent
Furman et al.

(10) Patent No.: US 8,960,007 B2
(45) Date of Patent: Feb. 24, 2015

(54) HANDHELD PROBE FOR TUBE INSPECTION USING APR

(75) Inventors: Dov Furman, Rehovot (IL); Harel Primack, Rishon LeZion (IL); Silviu Zilberman, Rishon LeZion (IL); Oded Barzelay, Givataim (IL)

(73) Assignee: Acoustic Eye, Ltd, Tel Aviv (IL)

( * ) Notice: Subject to any disclaimer, the term of this patent is extended or adjusted under 35 U.S.C. 154(b) by 133 days.

(21) Appl. No.: 13/403,984

(22) Filed: Feb. 24, 2012

(65) Prior Publication Data

US 2012/0227501 A1    Sep. 13, 2012

Related U.S. Application Data

(60) Provisional application No. 61/451,573, filed on Mar. 10, 2011.

(51) Int. Cl.
*G01N 29/00* (2006.01)
*G01N 29/22* (2006.01)

(52) U.S. Cl.
CPC ........ *G01N 29/226* (2013.01); *G01N 2291/044* (2013.01); *G01N 2291/2636* (2013.01)
USPC ............................................................ 73/627

(58) Field of Classification Search
None
See application file for complete search history.

(56) References Cited

U.S. PATENT DOCUMENTS

2006/0075730 A1\* 4/2006 Paxton et al. .................... 55/406
2008/0208505 A1\* 8/2008 Amir et al. ..................... 702/103

\* cited by examiner

*Primary Examiner* — Hezron E Williams
*Assistant Examiner* — Mark A Shabman
(74) *Attorney, Agent, or Firm* — Smith Rislet Temple Santos LLC; Gregory Scott Smith

(57) ABSTRACT

Exemplary embodiments of a handheld probe (HHP) of an Acoustic pulse reflectometry (APR) system are disclosed. Embodiments of the HHP can comprise a loudspeaker and microphone that are vibration isolated from each other and from the tube under test. In some embodiments the microphone can be isolated from the housing of the HHP. In other embodiments the housing of the HHP can be isolated from the loudspeaker. In another embodiment the housing of the probe can be isolated from the tube under test. Yet, some embodiments combine all of this isolation options. In such embodiment the loudspeaker is isolated from the housing, the housing is isolated from the tube under test, and the microphone is isolated from the housing, and so on. Isolation can be achieved by using materials that absorb vibration, material such as but not limited to rubber, foam, silicone, etc.

9 Claims, 2 Drawing Sheets

HANDHELD PROBE FOR TUBE INSPECTION USING APR

CROSS-REFERENCE TO RELATED APPLICATIONS

This is a non-provisional application for patent being filed in the United States Patent Office under 35 USC 111 and 37 CFR 1.53(b) and claiming priority under 35 USC 119(e) to the provisional application for patent filed in the United States Patent Office on Mar. 10, 2011, bearing the title of "HANDHELD PROBE FOR TUBE INSPECTION USING APR" and assigned Ser. No. 61/451,573, which application is incorporated herein by reference in its entirety.

BACKGROUND OF THE INVENTION

The present disclosure is in the technical field of Non Destructive Testing of tubes. More particularly, the present disclosure is related to the technical field of Acoustic Pulse Reflectometry (APR).

APR consists of sending an acoustic pulse into a tube to be inspected, and measuring any reflections that are created in the tube. Reflections are usually indications of defects in the tube. The reflections are processed and after proper interpretation can be used to identify defects, if they exist. Information on each defect can comprise the distance of the defect from the tube inlet and type of defect.

The sensitivity of an APR system depends on the Signal to Noise Ratio (SNR) which is achieved in the measurements. Small or distant defects create faint reflections, and when the SNR is low, these reflections are drowned in background noise, and cannot be detected. Therefore improving the SNR is a goal of any designer of an APR system.

BRIEF SUMMARY

SNR can be improved by increasing the intensity of the input signal, the transmitted acoustic signal. However, loudspeakers used to convert the electronic signal into an acoustic signal exhibits nonlinear distortions when driven at high levels.

One way to improve the performance of the loudspeaker is to improve the input electronic signal. An exemplary system to reduce the nonlinear distortion by processing the electronic signal is disclosed in a regular US Patent application publication number US 2011/0,166,808.

The current disclosure describes a novel method and system for improving the SNR by adapting the engagement of the electro/acoustic transducers (loudspeaker and microphone) within the handheld probe. The handheld probe comprises a loudspeaker, microphone and mounting hardware to be connected to a measured tube. The new configuration improves the transfer function of the acoustic wave from the loudspeaker to the tube and back to the microphone. As a result the SNR of the received reflected signal is improved.

These and other aspects of the disclosure will be apparent in view of the attached figures and detailed description. The foregoing summary is not intended to summarize each potential embodiment or every aspect of the present disclosure, and other features and advantages of the present disclosure will become apparent upon reading the following detailed description of the embodiments with the accompanying drawings and appended claims.

Furthermore, although specific embodiments are described in detail to illustrate the inventive concepts to a person skilled in the art, such embodiments are susceptible to various modifications and alternative forms. Accordingly, the figures and written description are not intended to limit the scope of the inventive concepts in any manner.

BRIEF DESCRIPTION OF THE DRAWINGS

Some examples of embodiments of the present disclosure will be understood and appreciated more fully from the following detailed description, taken in conjunction with the drawings in which.

DETAILED DESCRIPTION OF EMBODIMENTS OF THE INVENTION

Figure 1:
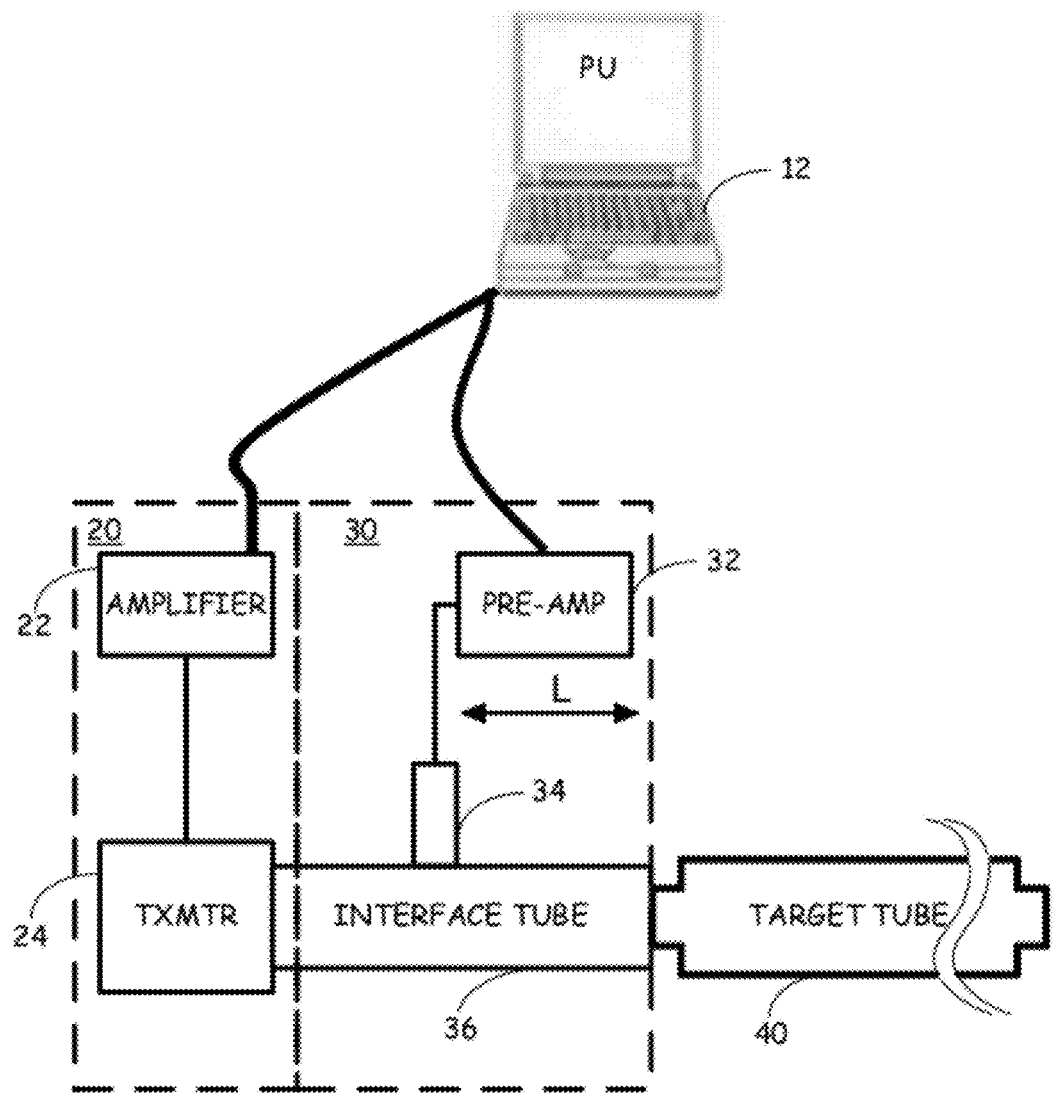
FIG. 1 shows a block diagram with relevant elements of an exemplary inspection system employing APR technology for the provision of innocuously-testing or inspection of tubes.
Figure 2:
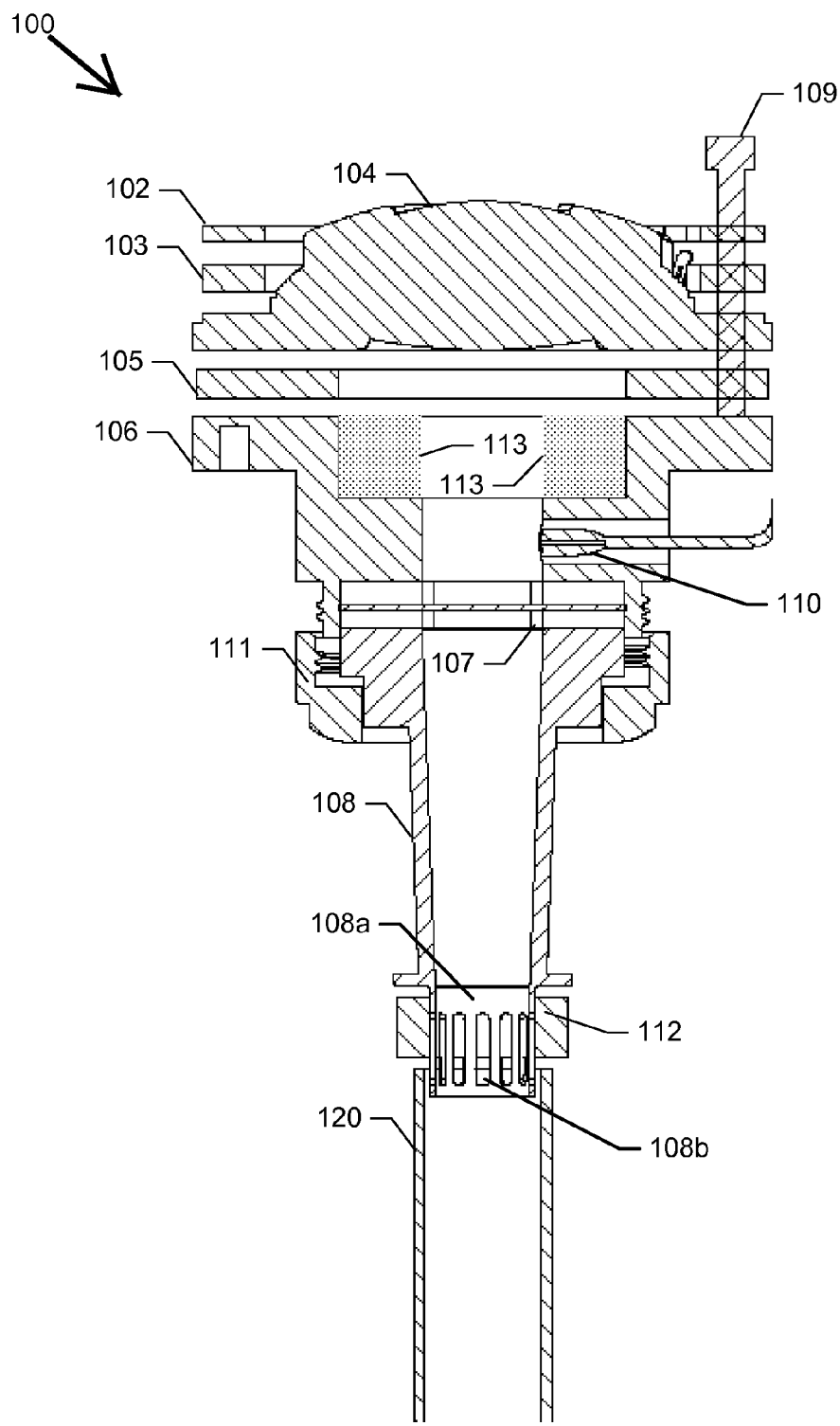
FIG. 2 illustrates a cross section view of an example of handheld probe.

Turning now to the figures in which like numerals represent like elements throughout the several views, different embodiments of the present disclosure are described. For convenience, only some elements of the same group may be labeled with numerals. The purpose of the drawings is to describe different embodiments and not for production. Therefore features shown in the figures are chosen for convenience and clarity of presentation only. It should be noted that FIG. 1 and FIG. 2 are for illustration purposes only and are drawn out-of-scale. Moreover, the language used in this disclosure has been principally selected for readability and instructional purposes, and may not have been selected to delineate or circumscribe the inventive subject matter, resort to the claims being necessary to determine such inventive subject matter.

Several exemplary embodiments of a real time innocuous inspection system based on the use of Acoustic Pulse Reflectometry (APR) technology are presented. An exemplary APR based inspection system for Non-Destructive Testing (NDT) of tubular systems has been described in detail in a U.S. Pat. No. 7,677,103B2 the content of which incorporated herein by reference.

In an APR handheld probe a transmitting element, a loudspeaker for example, and the receiving element, a microphone, for example, reside close to each other, in order to reduce the size and weight of the handheld probe. Further, the microphone also resides close to a tube that is under test. In addition, in order to improve the signal to noise ratio (SNR) high power transmitters are used.

We found that the combination similar to the above layout of a handheld probe of APR system reduces the SNR. Further, we found that contributing factors to reduction in the performance of an APR system can be vibration, acoustic and mechanical, that can travel via the housing of the handheld probe and received and converted into an electronic signal by the microphone. Another reason for poor performance can be a poor seal between the probe and tube under test, or mechanical vibrations transmitted from the tube under test.

In example of embodiments of a novel handheld probe of an APR system the acoustic elements are vibration isolated from each other and from the tube under test. In some embodiments the microphone can be isolated from the housing of the probe. In other embodiments the housing of the probe can be isolated from the loudspeaker. In another embodiment the housing of the probe can be isolated from the tube under test. Yet, some embodiments combine all this isolation options. In such embodiment the loudspeaker is isolated from the housing, the housing is isolated from the tube under test, and the microphone is isolated from the housing, and so on. Isolation can be achieved by using materials that absorb vibration, material such as but not limited to rubber, foam, silicone, etc.

FIG. 1 shows a block diagram with relevant elements of an example of an inspection system employing APR technology for the provision of innocuously-testing or inspection of tubes. The illustrated embodiment includes a signal injector 20 and a signal detector 30. The signal injector 20 is configured to inject a signal into a medium, or an interface tube 36, which acts as an interface to a target tube being tested 40. The signal can be an acoustic wave for example. The wave then propagates into the target tube 40. The signal detector 30 includes a sensor 34 that detects signals reflected back from the target tubes 40 into the interface tube 36. As illustrated in FIG. 1, the sensor 34 can be located at a distance L from the end of the interface tube 36. The signal injector 20 and signal detector 30 may operate as a stand-alone unit, a stand-alone unit that interfaces and/or reports information to other system, by an external processing unit 12 such as a personal computer, as well as other structures and/or configurations.

In a stand-alone configuration, a processing unit may be incorporated into the signal injector 20 and/or the signal detector 30. In such embodiments, the processing unit may be as simple as a microcontroller, an ASIC or even simply analog and/or digital control circuitry. The stand-alone unit may include a user interface for initiating a test sequence or, it may simply be activated by coupling the interface tube 36 to a tube under test 40. The recorded signal may be stored in internal memory and/or information regarding the detection may be displayed to a user in a variety of manners including the use of an LCD or even simple codes displayed using lights or numbers, or audible sounds such as error codes or certain tones or buzzers may also be used.

The exemplary inspection system that is shown in FIG. 1 can comprise the processing unit 12 that synthesizes an electronic signal which is transmitted through a transmitter 24 via an amplifier 22. The electronic signals converted into an acoustic wave by the transmitter 24, a loudspeaker, for example. The acoustic wave first propagates down an interface tube 36, where it is recorded by an exemplary pressure sensor 34. The acoustic wave then travels down a target tube 40, or a tube that is being subject to inspection, monitoring or examination.

Any change in the cross-section of the interior of the tube will cause a reflection that will propagate back up target tube 40 and interface tube 36, to be recorded by pressure sensor 34. The recoded signal can be amplified by a pre-amp 32, be converted into digital data and then stored, or information about such reflection being stored, by processing unit 12. The recorded reflections are analyzed by software applications being executed by processing unit 12 or another computing system, in order to identify the faults that created them, such as blockages (full or partial), pitting, general wall loss, bulges and holes.

Referring now to FIG. 2 that illustrates a cross section view of an example of an embodiment of handheld probe 100. The handheld probe (HHP) 100 can comprise a support ring 102 such as a metal ring; a vibration absorbing ring (VAR) 103, such as but not limited to a rubber ring; a transmitter, (loudspeaker) 104, a second VAR, such as a rubber ring 105; a housing 106, a washer 107; a short interface (adapter) tube (SIT) 108, held in place by a threaded retainer 111. The washer 107 can be a disk made of rubber. The SIT 108 can be a tube made of plastic. The cross section of SIT 108 can have a conical shape. The diameter of the ingress orifice of SIT 108 can fit the diameter of the egress orifice of the housing 106 while the egress orifice of the SIT 108 can have a diameter that fits the diameter of the tube under test 120.

The HHP 100 is kept as one unit by a plurality of screws 109 around the HHP 100, only one screw is illustrated in FIG. 2. The plurality of screws 109 keep the assembly together, by pressing against support metal ring 102 on one side and threading into housing 106 on the other. The middle of each screw shaft is smooth, so that the loudspeaker 104 is held only by the pressure of VAR 103 and 105. In this way it is isolated from creating any mechanical vibrations in the assembly. Further, the housing 106 is attached to a tube under test 120 via washer 107 and SIT 108. In some embodiments SIT 108 has a foam ring 112 which also isolates vibration between the SIT 108 of the HHP 100 and the tube 120, also providing a good seal. Furthermore, the washer 107 and the SIT 108 improve the matching between the HHP and the tube 120, isolate vibrations between the HHP and the tube 120.

In some embodiments, the egress edge of SIT 108 may comprise a "Diameter smoother" 108a. The "Diameter smoother" 108a can have a plurality of openings 108b around its wall. The openings can have different shapes, rectangles, circles, etc. The opening can reduce the reflections that are due to change in the cross-section of the interior of the space at the interface between the SIT 108 and the tube under test 120. Thus improving the SNR of the detected signal.

The acoustic signal created by loudspeaker 104 propagates into the housing 106 which contains a thick ring 113 of open celled foam located in a recess at the ingress of housing 106. As it propagates further it is recorded by microphone 110 inserted into housing 106 to be flush with the surface of the housing 106 and not protrude into the path of the acoustic wave. We found that the foam thick ring 113 improves the acoustic signal transferred from the loudspeaker 104 to the tube under test 120 in a manner which reduces nonlinear distortions.

Thus, the thick ring 113 in the path of the acoustic signal reduces nonlinear distortions considerably, enabling the loudspeaker 104 to be driven at higher levels than without this ring.

Further, we found that adding a thick ring 112 of open celled foam located in a recess at the egress of SIT 108 improves the acoustic interface with the tube under test 120 in a manner which reduces leakage of acoustic energy and reduces reflection from the interface.

Following are few examples of components that can be used in an exemplary HHP for inspecting tubes of 0.5" to 1.5", an exemplary loudspeaker 104 can be a Scanspeak D3004/66400. Exemplary rubber rings 103 and 105 can be made of foam rubber several millimeters in thickness, and an Exemplary thick ring 113 can have internal diameter 22 mm, external diameter 50 mm and thickness 20 mm. Different SIT 108 can be fitted interchangeably in between the housing 106 and the tube under test 120 in order to permit inspection of tubes of different diameters. SIT 108 can be easily replaced by unscrewing threaded retainer 111.

An exemplary housing 106, support ring 102 or any other rigid part can be made from metal or any other sufficiently rigid and strong material such high-strength plastic.

Exemplary embodiments of HHP 100 delivers improved SNR by creating acoustic signals of high intensity with a minimum of mechanical linkage between the loudspeaker and microphone, and a minimum of nonlinear distortion from the loudspeaker.

Yet in another embodiment, the loudspeaker 104 can be held in a floating and cushioned manner to prevent transferring mechanical vibrations to the structure holding it. Further the acoustic wave propagates in part of its path through a tunnel of open cell foam. These two means serve to reduce the creating of spurious mechanical signals by the loudspeaker and also reduce the nonlinear distortions created by the loudspeaker when it is driven at high levels. Together they enable the APR system to achieve high levels of SNR.

In the description and claims of the present disclosure, each of the verbs, "comprise", "include" and "have", and conjugates thereof, are used to indicate that the object or objects of the verb are not necessarily a complete listing of members, components, elements, or parts of the subject or subjects of the verb.

The present disclosure has been described using detailed descriptions of embodiments thereof that are provided by way of example and are not intended to limit the scope of the invention. The described embodiments comprise different features, not all of which are required in all embodiments of the invention. Some embodiments of the present disclosure utilize only some of the features or possible combinations of the features. Many other ramification and variations are possible within the teaching of the embodiments comprising different combinations of features noted in the described embodiments.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention. It will be appreciated by persons skilled in the art that the present invention is not limited by what has been particularly shown and described herein above. Rather the scope of the invention is defined by the claims that follow.

We claim:

1. A handheld probe (HHP) of an Acoustic pulse reflectometry (APR) system for measuring a tube under test, the HHP comprising:
    a. a rigid housing having a tunnel along the housing from an egress end of the housing;
    b. a microphone inserted in a wall of the housing;
    c. a loudspeaker associated with the ingress end of the housing via a first vibration absorbing ring (VAR);
    d. a short interface tube (SIT) associated with the egress end of the housing via a washer wherein the diameter of the ingress orifice of the SIT fits the diameter of the egress of the rigid housing and an egress section of the SIT is adapted to be entered to ingress of the tube under test; and
    e. an assembling mechanism comprising:
    a threaded retainer that associate the SIT with the housing;
    a second VAR located on the other side of the loudspeaker so that the loudspeaker is held between the first and the second VAR;
    a support metal ring on the other side of the second ring; and
    a plurality of pressuring elements that push the housing against the support metal ring to associate the components of the HHP into a single device; and
    wherein, an orifice defined by the first VAR, the tunnel of the housing, an orifice defined by the washer and the SIT form an opening between the loudspeaker and a tube under test and between the microphone and tube under test for reflected acoustic waves return from the tube under test.

2. The HHP of claim 1, wherein the microphone surface substantially flush with the internal surface of the housing.

3. The HHP of claim 1, wherein the first VAR is made of rubber.

4. The HHP of claim 1, wherein the rigid housing having, at its ingress orifice, a recess that carries a thick ring made of open cell foam.

5. The HHP of claim 1, wherein the SIT having, at its egress orifice, a recess that carries a thick ring made of open cell foam.

6. The HHP of claim 1, wherein the vibration are acoustic vibrations.

7. The HHP of claim 1, wherein the microphone is isolated from vibrations that are transferred in the wall of the housing.

8. The HHP of claim 1, wherein the pressuring elements are a plurality of screws that pass between the housing and the support ring, wherein the middle of each screw shaft is smooth.

9. The HHP of claim 1, wherein the egress section of the SIT has a Diameter smoother having a plurality of openings around its wall.

\* \* \* \* \*